United States Patent [19]

Hanessian et al.

[11] Patent Number: 4,764,605
[45] Date of Patent: Aug. 16, 1988

[54] PROCESS FOR SELECTIVELY DEACETYLATING ACETYL DERIVATIVES OF SACCHARIDES

[75] Inventors: Stephen Hanessian, Quebec, Canada; Masahiro Kagotani, Hyogo, Japan

[73] Assignee: Daicel Chemical Industries, Ltd., Osaka, Japan

[21] Appl. No.: 809,970

[22] Filed: Dec. 17, 1985

[51] Int. Cl.$^4$ .................... C07G 3/00; C07G 17/00; C07H 15/00; C07H 1/00
[52] U.S. Cl. .................................. 536/124; 536/18.5; 536/115
[58] Field of Search .................... 536/18.5, 124, 115

[56] References Cited

U.S. PATENT DOCUMENTS 4,474,946  9/1984  Umezawa et al. .................. 536/124

OTHER PUBLICATIONS

Shiue, et al.: United States Statutory Invention Registration H74, Filed: 2-24-83.
Kohn, et al.: J. American Chemical Society, vol. 86 (1964).

*Primary Examiner*—Ronald W. Griffin
*Assistant Examiner*—Nancy S. Carson
*Attorney, Agent, or Firm*—Sughrue, Mion, Zinn, Macpeak, and Seas

[57] ABSTRACT

A process for selectively deacetylating an acetyl derivative of a saccharide is described, comprising treating an acetyl derivative of a monosaccharide or oligosaccharide using a mixture of an aqueous solution of alkali metal hydroxide/aqueous hydrogen peroxide/organic solvent to selectively hydrolyze acetate bonds at specific positions in the molecule, and thereby obtain a partially hydrolyzed acetyl derivative of a saccharide.

20 Claims, No Drawings

PROCESS FOR SELECTIVELY DEACETYLATING ACETYL DERIVATIVES OF SACCHARIDES

FIELD OF THE INVENTION

This invention relates to a process for selectively hydrolyzing acetate bonds at specific positions in a molecule by treating acetyl derivatives of saccharides under specific hydrolyzing conditions.

BACKGROUND OF THE INVENTION

While many of saccharide derivatives are important as physiologically active substances, it is not easy to prepare them by synthetic means. Saccharides contain a plurality of hydroxyl groups as functional groups in the molecules. Generally, upon reacting a reagent with a saccharide, various reaction products having substituents at different sites are produced simultaneously as by-products, and the efficiency of obtaining a desired product is very low. In synthesizing derivatives from corresponding saccharides, processes via derivatives in which hydroxyl groups are converted into ester groups or ether groups have been employed. Among them, acetylation is particularly useful since relatively moderate conditions can be applied as the reaction conditions, and the reaction products are generally solvent-soluble. However, when an acetyl derivative is subjected to hydrolysis, the selectivity with respect to the position of the ester bonds to be hydrolyzed is poor, resulting in a plurality of products of different structures.

For the reasons as described above, in synthesizing a saccharide derivative having a desired structure, it is necessary, in addition to the reaction with a predetermined reagent, to repeat the steps of introducing protective groups to protect hydroxyl groups, then removing the protective groups, and separating and purifying the product. This necessiates long series of steps and renders it difficult to obtain a desired derivative in a high yield.

Accordingly, although it is very much desired from a practical point of view to discover a process capable of preparing, effectively and in a short series of steps, a monosaccharide or oligosaccharide having hydroxyl groups that can be reacted with oxygen atoms only on carbon atoms at specific positions, while other hydroxyl groups being protected by substituents, no practicable process has yet been found.

SUMMARY OF THE INVENTION

As the result of extensive studies, the inventors of the present invention have now discovered a process capable of selectively hydrolyzing the ester groups only on specific carbon atoms among several acetate bonds in acetylated saccharides and converting them to hydroxyl groups, and thus have accomplished the present invention.

More specifically, it has been found that a mixture of an aqueous solution of alkali metal hydroxide/aqueous hydrogen peroxide/organic solvent has a performance of selectively or preferentially hydrolyzing one or two ester bonds at specific positions among acetate bonds in acetylated monosaccharides or oligosaccharides.

Thus, in accordance with the present invention, a process is provided for selectively deacetylating an acetyl derivative of a saccharide, comprising treating an acetyl derivative of a monosaccharide or oligosaccharide using a mixture of an aqueous solution of alkali metal hydroxide/aqueous hydrogen peroxide/organic solvent to selectively hydrolyze acetate bonds at specific positions in the molecule, and thereby obtain a partially hydrolyzed acetyl derivative of a saccharide.

DETAILED DESCRIPTION OF THE INVENTION

The reagent solution employed in the process according to the present invention is relatively inexpensive and less dangerous as compared with conventional reaction procedures, and the reaction can be carried out with an ordinary reaction apparatus. The acetyl derivatives of saccharides to which the process according to the present invention is applicable include monosaccharides and oligosaccharides, in which hydrogen atoms of hydroxyl groups are partially or entirely substituted with acetyl groups. Examples of such monosaccharides can include methyl tetra-O-acetyl-α-D-glucopyranoside, penta-O-acetyl-α-D-glucopyranoside, penta-O-acetyl-β-D-glucopyranoside, methyl 4,6-O-benzylidene-2,3-di-O-acetyl-α-D-glucopyranoside, and methyl 4,6-di-O-benzyl-2,3-di-O-acetyl-α-D-glucopyranoside. The characteristic feature of the process according to the present invention is in the use of a mixture comprising an aqueous solution of alkali metal hydroxide/aqueous hydrogen peroxide/organic solvent as a reagent for hydrolysis.

As the alkali metal hydroxide, lithium hydroxide, sodium hydroxide, and potassium hydroxide can be used, with the lithium hydroxide being particularly preferred. The preferred amount employed is such that an equimolar or an amount slightly in excess of equimolar of the alkali metal hydroxide, with respect to the acetategroups to be hydrolyzed, is introduced into the reaction system. While there is no particular restriction, the concentration of the aqueous hydrogen peroxide is generally suitable from 10 to 50% and preferably about 30%. Adequate amount used is such that an equimolar amount or more and preferably about 10 to 20 equimolar amount of hydrogen peroxide is introduced to the alkali metal hydroxide used simultaneously. Organic solvents miscible with water are preferred and those usable herein include tetrahydrofuran, dioxane, dimethylacetamide, dimethylformamide, and dimethyl sulfoxide, with tetrahydrofuran being particularly suitable. While there is no particular restriction on the reaction temperature, it is preferred to carry out the reaction at from 0° C. to room temperature (e.g., about 20° to 30° C.).

Examples in which the process according to the present invention can be carried out advantageously are shown below, referring to the indicated structural schemes.

Acetate bond at the C2 position of methyl tetra-O-acetyl-α-D-glucopyranoside (1) is selectively hydrolyzed as in (2).

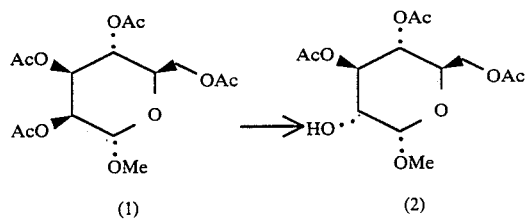

Acetate bonds at the C1 and C2 positions in penta-O-acetyl-α-D-glucopyranose (3) are selectively hydrolyzed as in (4).

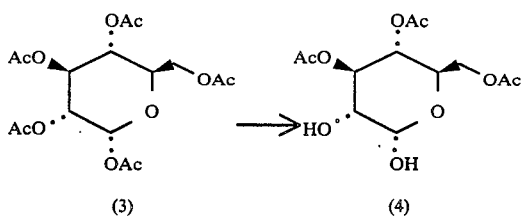

(3)    (4)

Acetate bond at the C2 position in methyl 4,6-O-benzylidene-2,3-di-O-acetyl-α-D-glucopyranoside (5) is selectively hydrolyzed as in (6).

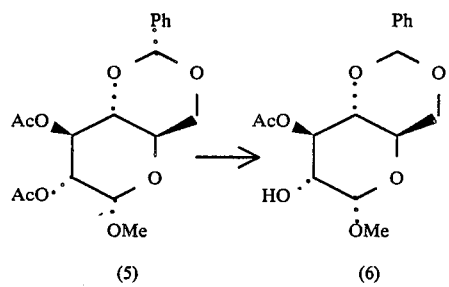

(5)    (6)

Acetate bond at the C1 position in octa-O-acetyl-α-D-cellobiose (7) is selectively hydrolyzed as in (8).

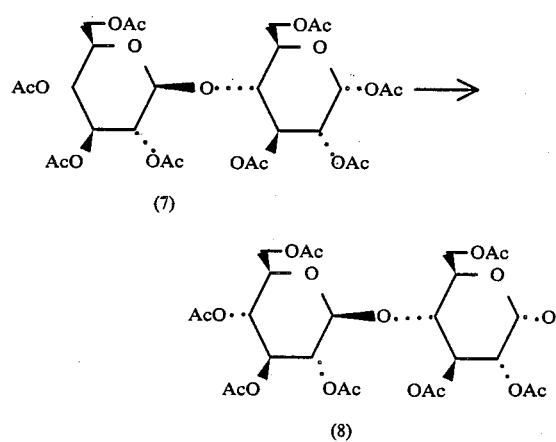

The present invention will now be described more specifically by referring to the following examples, but the invention is no way limited thereto. The names of the saccharide derivatives in the examples below are shown by attaching the name at the end of the number for the corresponding structural formula as described above.

EXAMPLE 1

Hydrolysis of methyl 2,3,4-tetra-O-acetyl-α-D-glucopyranoside (1):

Into a solution containing 360 mg of methyl 2,3,4,6-tetra-O-acetyl-α-D-glucopyranoside (1) dissolved in 10 ml of tetrahydrofuran, a liquid mixture of a 1N aqueous solution of lithium hydroxide (1.2 ml)/30% aqueous hydrogen peroxide (3.0 ml)tetrahydrofuran (15 ml) was added at 0° C. while stirring. After reacting them at 0° C. for one hour and then at room temperature for 30 minutes, 3 ml of an aqueous saturated solution of sodium thiosulfate was added at 0° C. After distillating off the tetrahydrofuran under reduced pressure at an ambient temperature, the residual liquid was extracted with 50 ml of ethyl acetate and the extract was washed with 30 ml of a saturated brine water and dried over anhydrous magnesium sulfate.

After distilling off the solvent under reduced pressure, the residue was subjected to column chromatography (fixed phase: silica gel, solvent: hexane/ethyl acetate=½) to separate and purify the starting material and the product. As the first distillate, the material (1) was recovered in an amount of 159 mg (percent recovery: 44.2%). As the second distillate, 163 mg of a mixture of metyl 3,4,6-tri-O-acetyl-D-glucopyranoside (2) and methyl 2,4,6-tri-O-acetyl-D-glucopyranoside (9/1) was obtained. The percent yield was 50.9%, which corresponded to 91.2% percent yield based on the reacted material (1). The properties and the results of analysis for the product (2) are shown below.

Configuration: Syrup $^1$H NMR spectrum, α-methyl 3,4,6-tri-O-acetyl-D-glucopyranoside (CDCl$_3$, ppm);

5.24 (t, J=8.4 Hz, 1H, H3), 4.99 (t, J=8.4 Hz, 1H, H4), 4.86 (d-d, J=3.8 and 8.4 Hz, 1H, H2), 4.83 (d, J=3.8 Hz, 1H, H1) 4.29 (d-d, J=4.7 and 10.0 Hz, 1H, H6) 4.07 (d-d, J=2.0 and 10.0 Hz, 1H, H6') 3.96 (m, J=4.7, 20 and 8.4 Hz, 1H, H5) 3.475 (s, 3H, —OMe), 2.10 (s, 3H, —OAc), 2.08 (s, 3H, —OAc), 2.03 (s, 3H, OAc), 3.66 (br, 1H, —OH)

A methyl signal in the methoxy group of α-methyl 2,4,6-tri-O-acetyl-D-glucopyranoside was observed at 3.41 ppm.

IR (liquid film: cm$^{-1}$);

3460 (m, νOH), 1740 (s, νCO), 1230 (s), 1030 (s).

The structure of the product (2) was further confirmed by treating the same in pyridine with d$_3$-acetyl chloride into d$_3$-acetylated tetraacetate body, and from the fact that the hydroxyl group at the C2 position is d$_3$-acetylated due to the chemical shift of the acetyl group in the proton NMR spectrum based on the literature (D. Horton and J. H. Lauterbach, J. Org. Chem., Vol. 34, 1969, pp. 86–92). The procedures are as below. The product (2) (50 mg) was dissolved in 2 ml of dry pyridine, to which 0.1 ml of d$_3$-acetyl chloride was added at 0° C. After leaving the reaction mixture at −15° C. overnight and completing the reaction, the pyridine was removed under reduced pressure, and the residue was extracted with 30 ml of ethyl acetate. The extract was washed with 2N hydrochloric acid, and then with saturated brine water, and thereafter dried over anhydrous magnesium sulfate. The solvent was distilled off under reduced pressure, and the residue was subjected to column chromatography (silica gel, solvent: hexane/ethyl acetate=1/1) to isolate and purify the tetraacetate body. The yield was 48 mg and the percent yield was 85%. Proton NMR spectrum of the tetraacetate body (in CDCl$_3$) showed 3H signals each at δ=2.099, 2.027 and 2.014 which corresponded to acetyl groups at the 1, 4, and 3 positions, respectively, and it was thus confirmed that the hydroxyl group at the 2-position was d$_3$-acetylated.

EXAMPLE 2

Hydrolysis of penta-O-acetyl-α-D-glucopyranose (3):

In the similar procedures as in Example 1, to a solution containing 600 mg of penta-O-acetyl-α-D- glucopyranose (3) dissolved in 10 ml of tetrahydrofuran, a liquid mixture of a 1N aqeous solution of lithium hydroxide (2 ml)/30% aqueous hydrogen peroxide (5 ml)/tetrahydrofuran (30 ml) was added at 0° C. After reacting them at 0° C. for 2 hours, 10 ml of an aqueous saturated solution of sodium thiosulfate was added at 0° C.

Then, the products were isolated and purified by the similar procedures as in Example 1.

356 mg of the starting material (3) was recovered and 217 mg of the product, 3,4,6-tri-O-acetyl-D-glucose (4) was obtained. The percent yield was 40.5%, which corresponded to 99% percent yield based on the reacted starting material (3).

Chemical properties of (4): configuration: syrup, specific rotary power; $[\alpha]_D^{20} = +89.7°$ (c=2.75, CHCl$_3$), $^1$H-NMR in CDCl$_3$, $\delta$, internal standard, TMS;

5.32 (d, J=4 Hz, 1H, H1), 5.30 (t, J=10 Hz, 1H, H3), 5.18–4.90 (m, 2H), 4.77 (m, 1H, H5) 2.09–4.03 (m, 3H), 3.69 (d·d, J=4 and 10 Hz, 1H, H2), 2.09 (s, 6H), 2.04 (s, 3H)

IR (liquid film, cm$^{-1}$); 3440 (m, $\nu$OH), 2940 (w), 1740 (s, $\nu$CO), 1360 (m), 1230 (s), 1030 (s).

The structure of the product (4) was confirmed by methylating the hydroxyl group using diazomethane trifluoroborate etherate to transform to methyl 2-methyl-3,4,6-tri-O-acetyl-α-D-glucopyranoside, which is a known compound, followed by measuring the melting point and the specific rotary powder, based on the literature (A. F. Bochknov et al, *Carbohyd. Res.*, Vol. 30, p. 418 (1973)). Melting point: 120°–121° C. (observed), 119°–120° C. (lit), Specific rotary power: $[\alpha]_D^{20} = 157°$ (observed), 148° (lit). [CHCl$_3$, c=1.04]

EXAMPLE 3

Hydrolysis of methyl 4,6-O-benzylidene-2,3-di-O-acetyl-α-D-glucopyranoside (5):

To a solution containing 432.8 mg of methyl 4,6-O-benzylidene-2,3-di-O-acetyl-α-D-glucopyranoside (5) dissolved in 15 ml of tetrahydrofuran, 20 ml of a mixture of 1N lithium hydroxide (1.4 ml)/30% aqueous hydrogen peroxide (3.5 mg)/tetrahydrofuran (20 ml) was added at 0° C. After reacting them at 0° C. for one hour and at room temperature for 30 minutes, 5 ml of an aqueous saturated sodium thiosulfate was added at 0° C. They were treated hereinafter by the similar procedures as those in Example 1. 120 mg of the starting material (5) was recovered and 170 mg of methyl 4,6-O-benzylidene-3-O-acetyl-α-D-glucopyranoside (6) was obtained as the product. The percent yield was 44.4% which corresponded to 61.5% percent yield based on the reacted material (5). In addition, 77 mg of 4,6-O-benzylidene-α-D-glucopyranoside (23% percent yield) was obtained.

The properties and the results of analysis for the product (6) are shown below.

Configuration: acicular crystal, m.p.: 173.5°–174.5° C. (recrystallized from hexane-ethanol), literature value: 174° C., $[\alpha]_D^{20} = +112°$ (c=0.9, CHCl$_3$), literature value $[\alpha]_D^{14} = +110°$ (c=0.85, CHCl$_3$), $^1$H-NMR(CDCl$_3$, $\delta$);

7.2–7.4 (m, 5H), 5.49 (s, 1H, proton at benzyl position), 5.33 (t, J=9 Hz, 1H, H3), 4.80 (d, J=3.5 Hz, 1H, H1), 4.30 (d·d, J=3 and 9 Hz, 1H, H6), 3.92–3.53 (m, 4H), 3.47 (s, 3H, —OMe), 2.12 (s, 3H, —OAc), 2.30 (1H, —OH).

IR (KBr, cm$^{-1}$); 3400 (m, $\nu$OH), 1740 (S, $\nu$CO), 1370 (s), 1250 (s), 750 (s), 700 (s), (see E. I. Boarne, M. Stacey, C. E. M. Tatlow, T. C. Tatlow, *J. Chem. Soc.*, 826 (1951)).

EXAMPLE 4

Hydrolysis of octa-O-acetyl-α-D-cellobiose (7):

600 mg of octa-O-acetyl-α-D-cellobiose (7) was dissolved in a mixed solution of tetrahydrofuran (15 ml)/methylene chloride (15 ml), to which was added a liquid mixture of 1N lithium hydroxide (1 ml)/30% aqueous hydrogen peroxide (2.5 ml)/tetrahydrofuran (15 ml) at room temperature under stirring. After reacting them at room temperature for one hour, 3 ml of an aqueous saturated solution of sodium thiosulfate was added at 0° C. Thereafter, they were treated in the similar procedures as those in Example 1 except for using 50 ml of chloroform for extraction. 94 mg of the starting material (7) was recovered, and 324.5 mg of the product, 2,3,6,2',3',4',6'-hepta-O-acetyl-α-D-cellobiose (8) was obtained. The percent yield was 58%.

The properties and the results of the analysis for the product (8) are shown below.

Configuration: acicular crystal (ethanol/hexane), m.p.: 208°–209° C., literature value: 209°, $[\alpha]_D^{20} = +32.8° \rightarrow +22.3°$ (24 h, c=2.28, pyridine), literature value $[\alpha]_D^{20} = +33.4° \rightarrow +23°$ (24 h, c=2.22, pyridine) $^1$H NMR (CDCl$_3$, $\delta$, TMS); acetoxy group signals, 2.14 (s, 3H), 2.11 (s, 6H), 2.06 (s, 6H), 2.04 (s, 3H), 2.02 (s, 3H)

IR (KBr, cm$^{-1}$); 3480 (m, $\nu$OH), 1750 (s, $\nu$CO), 1435 (m), 1370 (m), 1230 (s) (see R. H. Rowell and M. S. Feather, *Carbohyd. Res.*, 4, p. 486 (1967)).

While the invention has been described in detail and with reference to specific embodiments thereof, it will be apparent to one skilled in the art that various changes and modifications can be made therein without departing from the spirit and scope thereof.

What is claimed is:

1. A process for selectively deacetylating an acetyl derivative of a monosaccharide or oligosaccharide, comprising treating an acetyl derivative of a monosaccharide or oligosaccharide with a mixture of an aqueous solution of alkali metal hydroxide/aqueous hydrogen peroxide/organic solvent to selectively hydrolyze acetate bonds at specific positions in the molecule, and thereby obtain a partially hydrolyzed acetyl derivative of a monosaccharide or oligosaccharide.

2. A process as in claim 1, wherein the alkali metal hydroxide is lithium hydroxide.

3. A process as in claim 1, wherein the alkali metal hydroxide is present in an equimolar amount or an amount slightly in excess of equimolar with respect to the acetate groups to be hydrolyzed.

4. A process as in claim 2, wherein the lithium hydroxide is present in an equimolar amount or an amount slightly in excess of equimolar with respect to the acetyl group to be hydrolyzed.

5. A process as in claim 1, wherein the concentration of the aqueous hydrogen peroxide is from 10 to 50%.

6. A process as in claim 2, wherein the concentration of the aqueous hydrogen peroxide is from 10 to 50%.

7. A process as in claim 3, wherein the concentration of the aqueous hydrogen peroxide is from 10 to 50%.

8. A process as in claim 4, wherein the concentration of the aqueous hydrogen peroxide is from 10 to 50%.

9. A process as in claim 1, wherein the organic solvent is selected from the group consisting of tetrahydrofuran, dioxane, dimethylacetamide, dimethylformamide, and dimethyl sulfoxide.

10. A process as in claim 2, wherein the organic solvent is selected from the group consisting of tetrahydrofuran, dioxane, dimethylacetamide, dimethylformamide, and dimethyl sulfoxide.

11. A process as in claim 3, wherein the organic solvent is selected from the group consisting of tetrahydrofuran, dioxane, dimethylacetamide, dimethylformamide, and dimethyl sulfoxide.

12. A process as in claim 4, wherein the organic solvent is selected from the group consisting of tetrahydrofuran, dioxane, dimethylacetamide, dimethylformamide, and dimethyl sulfoxide.

13. A process as in claim 9, wherein the organic solvent is tetrahydrofuran.

14. A process as in claim 10, wherein the organic solvent is tetrahydrofuran.

15. A process as in claim 11, wherein the organic solvent is tetrahydrofuran.

16. A process as in claim 12, wherein the organic solvent is tetrahydrofuran.

17. A process as in claim 1, wherein the process is carried out at a temperature of from 0° to about 30° C.

18. A process as in claim 2, wherein the process is carried out at a temperature of from 0° to about 30° C.

19. A process as in claim 3, wherein the process is carried out at a temperature of from 0° to about 30° C.

20. A process as in claim 4, wherein theprocess is carried out at a temperature of from 0° to about 30° C.

* * * * *